(12) United States Patent
Onishi et al.

(10) Patent No.: US 7,235,707 B2
(45) Date of Patent: Jun. 26, 2007

(54) ABSORBENT ARTICLE FOR REDUCING URINE ODOR

(75) Inventors: Kazuaki Onishi, Kagawan-ken (JP); Takayuki Hisanaka, Kagawan-ken (JP)

(73) Assignee: Uni-Charm Corporation, Ehime-Ken (JP)

( * ) Notice: Subject to any disclaimer, the term of this patent is extended or adjusted under 35 U.S.C. 154(b) by 366 days.

(21) Appl. No.: 10/348,332

(22) Filed: Jan. 22, 2003

(65) Prior Publication Data

US 2003/0171726 A1    Sep. 11, 2003

(30) Foreign Application Priority Data

Jan. 24, 2002    (JP)    ............ 2002-015147

(51) Int. Cl.
*A61F 13/15* (2006.01)
*A61F 13/20* (2006.01)
*A01N 25/34* (2006.01)

(52) U.S. Cl. ............ 604/359; 604/360; 424/404; 428/905

(58) Field of Classification Search ............ None
See application file for complete search history.

(56) References Cited

U.S. PATENT DOCUMENTS

| | | | | |
|---|---|---|---|---|
| 5,639,470 A | * | 6/1997 | Ishibashi et al. ............ | 424/439 |
| 5,932,495 A | | 8/1999 | Boney et al. | |
| 6,165,797 A | * | 12/2000 | Halstead ............ | 436/128 |
| 6,252,003 B1 | * | 6/2001 | Kuwahara et al. ............ | 525/242 |
| 6,333,109 B1 | * | 12/2001 | Harada et al. ............ | 428/402 |
| 6,359,032 B1 | * | 3/2002 | Kuwahara et al. ............ | 523/201 |
| 6,833,487 B2 | * | 12/2004 | Pesce et al. ............ | 604/358 |
| 2004/0122385 A1 | * | 6/2004 | Morman et al. ............ | 604/359 |

FOREIGN PATENT DOCUMENTS

| | | | |
|---|---|---|---|
| JP | 62-106767 | | 5/1987 |
| JP | 04289274 A | * | 10/1992 |
| JP | 5-59601 | | 3/1993 |
| JP | 6-57238 | | 8/1994 |
| JP | 8-60509 | | 3/1996 |
| JP | 8-164159 | | 6/1996 |
| JP | 8-191857 | | 7/1996 |
| JP | 8-196559 | | 8/1996 |
| JP | 8-322876 | | 12/1996 |
| JP | 9-23776 | | 1/1997 |
| JP | 9-28729 | | 2/1997 |
| JP | 9-51913 | | 2/1997 |
| JP | 9-206323 | | 8/1997 |
| JP | 9-234167 | | 9/1997 |
| JP | 9-299271 | | 11/1997 |
| JP | 10-264276 | | 10/1998 |
| JP | 11-128259 | | 5/1999 |
| JP | 11-217453 | | 8/1999 |
| JP | 11-241204 | | 9/1999 |
| JP | 11-302955 | | 11/1999 |
| JP | 11-318791 | | 11/1999 |
| JP | 2000-152957 | | 6/2000 |
| JP | 2000-189454 | | 7/2000 |
| JP | 2000-342624 | | 12/2000 |
| JP | 2001-9953 | | 1/2001 |
| JP | 2001-104041 | | 4/2001 |
| JP | 2001-309968 | | 11/2001 |
| JP | 2001-327534 | | 11/2001 |
| JP | 2002-651 | | 1/2002 |
| JP | 2002-65735 | | 3/2002 |
| JP | 2002-67206 | | 3/2002 |
| JP | 2002-126002 | | 5/2002 |
| JP | 2002-153510 | | 5/2002 |
| JP | 2002-159531 | | 6/2002 |
| JP | 2002-238949 | | 8/2002 |
| JP | 2002-300848 | | 10/2002 |
| JP | 2002-301105 | | 10/2002 |
| JP | 2002-325798 | | 11/2002 |
| WO | WO 98/27261 | | 6/1998 |

OTHER PUBLICATIONS

EAST- Derwent Abstract of JP 04289274A, published Oct. 14, 1992.*
Database WPI—Derwent Publications Ltd.—Publication No. XP002243093—Abstract of Japanese Application No. 11 332778, Published Dec. 7, 1999.
Database WPI—Derwent Publications Ltd.—Publication No. XP002243094—Abstract of Japanese Application No. 62 038285, Published Feb. 19, 1987.
Database WPI—Derwent Publications Ltd.—Publication No. XP002243095—Abstract of Japanese Application No. 2001 172868, Published Jun. 26, 2001.

* cited by examiner

*Primary Examiner*—Tatyana Zalukaeva
(74) *Attorney, Agent, or Firm*—Lowe Hauptman & Berner

(57) ABSTRACT

An absorbent article contains a hydrophilic fiber processed by a water-soluble deodorant containing a graft polymer having a deodorant functional group. This constitution ensures to have large deodorizing function per unit weight, compared to a particulate deodorant. Consequently, the constitution allows to decrease a weight of the deodorant and to excel in deodorizing function. Moreover, it is unnecessary to fix the deodorant and easy to compound with the absorbent article. Therefore, it allows to obtain an absorbent article having excellent aesthetics and cleanness.

8 Claims, 6 Drawing Sheets

Fig. 3

<u>< amines(ammonia) ></u>

$R_1 - COOH + NH_3 \rightarrow R_1 - COO^- NH_4^+$ $R_2 - CO_3H + NH_3 \rightarrow R_1 - CO_3^- NH_4^+$ <u>< lower fatty acids(isovaleric acid) ></u>

$R_1 - NH_2 + (CH_3)_2 CHCH_2 COOH \rightarrow R_1 - NH_3^+ + (CH_3)_2 CHCH_2 COO^-$ <u>< sulfur compounds(hydrogen sulfide) ></u>

$2(R_1 - NH_2 + H_2S) \rightarrow (R_1 - NH_3^+)_2 S^{2-}$

<u>< aldehydes ></u>

$R_1 - NH_2 + R_2CH = O \rightarrow R_1 - NH \rightarrow R_1 - N = CH - R_2 + H_2O$
$\phantom{R_1 - NH_2 + R_2CH = O \rightarrow R_1 - NH \rightarrow R_1 - N =} |$
$\phantom{R_1 - NH_2 + R_2CH = O \rightarrow R_1 - NH \rightarrow} R_2 - CH - OH$

ABSORBENT ARTICLE FOR REDUCING URINE ODOR

BACKGROUND OF THE INVENTION

1. Technical Field

The present invention relates to an absorbent article having a deodorizing function.

2. Related Art

An absorbent article such as an incontinence pad, a paper diaper, etc. and the deodorizing action are inseparably related, and the absorbent article provided with excellent deodorizing function has been continuously developed. Many attempts to add the deodorizing function to an absorbent article have been made, and, among them, compounding of particulate deodorant with the absorbent article has been frequently examined. Specifically, these attempts include adding materials having the deodorizing function such as zeolite, activated carbon, charcoal, silica gel, activated alumina, molecular sieve, cyclodextrin, and the like to a absorbent article. For example, Japanese Patent Laid-Open Publication No Hei 2-307528 discloses a technique of forming an absorbent sheet having a particulate deodorant by using a binder. Japanese Patent Laid-Open Publication No. Hei 8-176338 discloses a technique of compounding a particulate deodorant to the inside of absorbent resin particles. Furthermore, Japanese Patent Laid-Open Publication No. 2000-350745 discloses a technique for compounding particulate deodorant with hydrophilic fiber without water-swelling property to form a paper sheet. Furthermore, a number of liquid deodorants such as plant extracts and the like have been introduced. Thus, it is very important to constitute an absorbent article by skillfully compounding deodorant with absorbent materials. That is, using a suitable deodorant, it is important to compound it appropriately to an absorbent article. That is, it is necessary to appropriately compound a suitable deodorant with absorbent products (articles), thus the deodorizing function thereof being greatly influenced by these factors.

However, in these conventional examples, when the particulate deodorant is used for an absorbent article, the deodorizing effect is proportional to the amount thereof added so that it is necessary to add the particulate deodorant in a large quantity. However, since the particulate deodorant itself is incapable of immobilizing itself to the absorbent (compounding itself with the absorbent article) so as to be liable to falling away, it is necessary to immobilize the particulate deodorant by any means. In this regard, in Japanese Patent Laid-Open Publication No. Hei 2-307528, particulate deodorant is immobilized using binder. In this case, the binder covers up the particulate deodorant to decrease the contact area thereof with offensive odor, leading to the reduction in the deodorizing function, most likely resulting in weakening the deodorizing effect of absorbent article compounded with said deodorant. Furthermore, in Japanese Patent Laid-Open Publication No. Hei 8-176338, the particulate deodorant is placed in the inside of absorbent resin particles, so that the deodorizing function of particulate deodorant is reduced, most likely resulting in decreasing the deodorizing effect of the absorbent body compounded with said deodorant. Moreover, in Japanese Patent Laid-Open Publication No. 2000-350745, activated carbon is used as a deodorant. Activated carbon is black so that it most likely reduces the clean feeling and aesthetics of an absorbent article compounded wit said deodorant. Furthermore, when particulate deodorant of physical absorbent type such as activated carbon remains long in body fluid, moisture enters pores for absorbing offensive odor to reduce the deodorizing function thereof, most likely resulting in weakening the deodorizing effect of absorbent article compounded with said deodorant.

Furthermore, among conventionally introduced liquid deodorants, there are only few deodorants having sufficient function to deodorize the offensive odor of body fluid (urine in particular) so that it is necessary to add them in a large quantity. As a result, the relative volume of the absorbent body is reduced, thereby deteriorating the absorption capacity of the absorbent article produced by compounding the absorbent body, hardening the absorbent body to make it fragile, most likely worsening the wearing feeling and form stability thereof.

The present invention has been made in consideration of the above-described problems. It is an object of the present invention to provide an absorbent article excellent in the absorption capability and aesthetics, and having the deodorizing function with the cleanliness feeling.

SUMMARY OF THE INVENTION

To solve the aforementioned problems, an absorbent article in accordance with the present invention includes a hydrophilic fiber processed by a water-soluble deodorant containing a graft polymer having a deodorant functional group. This constitution ensures to have a large surface area in the surfaces of fibers, which is necessary for adsorbing odor components, compared to a particulate deodorant. Consequently, the constitution allows to decrease a weight of the deodorant and to excel in deodorizing function. Moreover, it is unnecessary to fix the deodorant and easy to compound with the absorbent article. Therefore, it allows to obtain an absorbent article having excellent aesthetics and cleanness.

Specifically, the present invention provides a deodorant, absorbent article as follows. Firstly, the present invention provides an absorbent article, comprising a hydrophilic fiber processed by a water-soluble deodorant. Since the hydrophilic fiber is processed by the water-soluble deodorant, the absorbent article has characteristics such that the compatibility is good each other and that the absorbent article has excellent deodorizing function. When the water-soluble deodorant is coated onto the hydrophilic fiber, for example, the water-soluble deodorant is sprayed onto the hydrophilic fiber and dried, the sprayed solution is thinly spread over the fibers, thereby enlarging a specific surface area, and therefore, it is thought to be preferable. Contrary to the particulate deodorant, the deodorant used for the present invention is easily combined with the fiber, and it is not necessarily need to use a binder and so on for keeping the deodorant itself in the absorbent article. Moreover, since the deodorant is in the form of an aqueous solution and so on, it has advantage that the deodorant easily spreads onto the fibers so as to easily perform penetration processing. Furthermore, when the fiber itself has water-swelling property or water-retaining amount, for example, it is possible to add deodorizing function to a urine absorber itself.

Moreover, an absorbent article in accordance with the present invention may be characterized by that the water-soluble deodorant comprises a compound having at least one of a cation exchange group and an anion exchange group. The features have such characteristic to improve adsorbing capability and retention capability so as to excel in deodorizing function. It is not necessary for the water-soluble deodorant to contain both exchange groups. However, when the water-soluble deodorant contains both exchange groups, in general, it is thought that there are a plurality of urine-odor components and it is thought to absorb odor components having different properties at the same time by having different exchange groups. Therefore, suppose the absorbent article absorbs a plurality of main odor components, which serve as cause, it is possible to prevent odor regardless of kinds of odor.

An absorbent article in accordance with the present invention may be characterized by that the absorbent article contains a water-soluble deodorant containing a compound having at least one of a cation exchange group and an anion exchange group, wherein the cation exchange group comprises at least one of sulfonic acid group and carboxylic group, and the anion exchange group comprises an amino group. Since the absorbent article has the exchange group for efficiently absorbing a urine-odor component, the absorbent article has characteristics to efficiently eliminate odor.

Moreover, an absorbent article in accordance with the present invention may be characterized by that the absorbent article contains a water-soluble deodorant containing a compound having at least one of a cation exchange group and an anion exchange group wherein at least one of the cation exchange group and the anion exchange group is bonded to a side chain of one of monosaccharide and oligosaccharide.

An absorbent article in accordance with the present invention comprises a hydrophilic fiber processed by a water-soluble deodorant. However, the absorbent article may be characterized by that the water-soluble deodorant is a deodorant obtained by graft polymerization.

An absorbent article in accordance with the present invention comprises a hydrophilic fiber processed by a water-soluble deodorant. However, the absorbent article may be characterized by having 100 parts by weight of a hydrophilic fiber substrate and 0.05 to 10 parts by weight of the water-soluble deodorant. Further preferably, the absorbent article may contain 0.1 to 5 parts by weight of the water-soluble deodorant. The absorbent article has characteristics to excel in deodorizing function by a small amount of the deodorant. An absorbent article in accordance with the present invention may be characterized by that with respect to 100 gram of water-retaining amount per each piece of the product, an amount of the deodorant may range from 0.005 to 1 gram, and preferably 0.01 to 0.5 gram.

An absorbent article in accordance with the present invention comprises a hydrophilic fiber processed by a water-soluble deodorant. However, the absorbent article may be characterized by that the hydrophilic fiber comprises at least one of a cellulose fiber, an acrylic fiber, an acetate fiber, a fibrous polyacrylate salt and any of the combination thereof. When these fibers are used in diapers and so on, the fibers may keep suitable safety and mechanical property in accordance with the functions. Since these fibers have water swelling property, the fibers can contain, for example, urine, which is cause of urine odor, and therefore, it has characteristics to be capable of efficiently eliminating odor. Moreover, it may be characterized by that the hydrophilic fibers may have water-retaining amount of at least 1 gram per gram. Preferably, the water-retaining amount ranges from 1 to 5 gram per gram, and, further preferably, from 1 to 10 gram per gram.

An absorbent article in accordance with the present invention comprises a hydrophilic fiber processed by a water-soluble deodorant. However, the absorbent article may be characterized by that the absorbent article is capable of absorbing at least one urine-odor component. Further, the absorbent article may be characterized by that the urine-odor component comprises a Lewis base component and a Lewis acid component. Moreover, the absorbent article may be characterized by that the Lewis base component comprises an amine and the Lewis acid component comprises at least one of a lower fatty acid, a sulfur compound and an aldehyde. (In general, aldehyde is considered as a neutral component. However, it is expressed in accordance with kinds of adsorbing deodorant herein.) Since the absorbent article absorbs a plurality of components having different property, it has characteristics that to eliminate urine odor becomes more efficient. Therefore, the absorbent article in accordance with the present invention is suitably used for a diaper.

The present invention may provide a diaper comprising an absorbent article, comprising a hydrophilic fiber processed by a water-soluble deodorant.

Further, the present invention may provide a hydrophilic fiber comprising a water-soluble deodorant containing a compound having a cation exchange group and an anion exchange group wherein the hydrophilic fiber is processed by the water-soluble deodorant.

Furthermore, the present invention may provide an absorbent article wherein each of deodorizing ratios of dimethylamine, acetaldehyde, and n-butyric acid is at least 50 percent. Incidentally, a period for achieving the deodorizing ratio of at least 50 percent is preferably shown as those in a Table mentioned later (for example, Table 5. It is thought that urine-order components contain each of dimethylamine, acetaldehyde, and n-butyric acid and that to eliminate odor of these compounds limits the urine odor. Incidentally, it is conception to include the case that these compounds are generated by chemical reaction or other change of derivatives of the three compounds in the neighborhood of the absorbent article. Further, the deodorizing ratio is calculated by a formula as follows,

[(a gas concentration of a blank–a gas concentration of each sample)/a gas concentration of the blank]×100

The deodorizing ratio is expressed by percentage. (Each sample refers to any of the aforementioned compound.)

BRIEF DESCRIPTION OF DRAWINGS

FIG. 3 shows chemical reactions for describing deodorizing function in accordance with the present invention.

PREFERRED EMBODIMENTS OF THE INVENTION

The present invention is described in detail hereinafter. However, the present invention is not limited thereto.

<Water-Soluble Deodorant>

The water-soluble deodorant may refer to a deodorant which is capable of becoming an aqueous solution or an emulsion having deodorizing function. The water-soluble deodorant may be a substance for preventing odor by absorbing and/or decomposing odor components such as surrounding urine odor through absorbing and/or deodorizing components. Such deodorant, for example, may contain a compound having at least one of a cation exchange group and an anion exchange group. The cation exchange group may contain at least one of sulfonic acid group and carboxylic group, and the anion exchange group contain an amino group. Such deodorant may be produced by performing graft polymerization such that the aforementioned compound containing at least one of the cation exchange group and the anion exchange group is bonded to a side chain of monosaccharide or oligosaccharide. The monosaccharide includes, for example, glucose, and the oligosaccharide includes sucrose. The graft polymerization refers to a polymerization for bonding compounds by energy such as heat, light and so on. The graft polymerization includes a graft polymerization by radioactive ray.

Figure 1A:
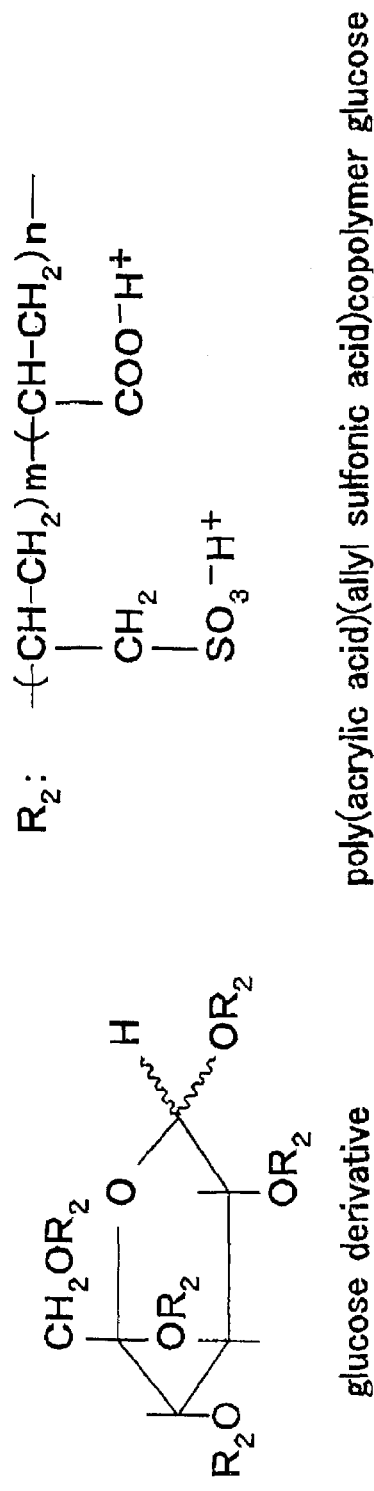
FIG. 1(a) and FIG. 1(b) are schematic view of deodorants, which may be used in the present invention.
Figure 1B:
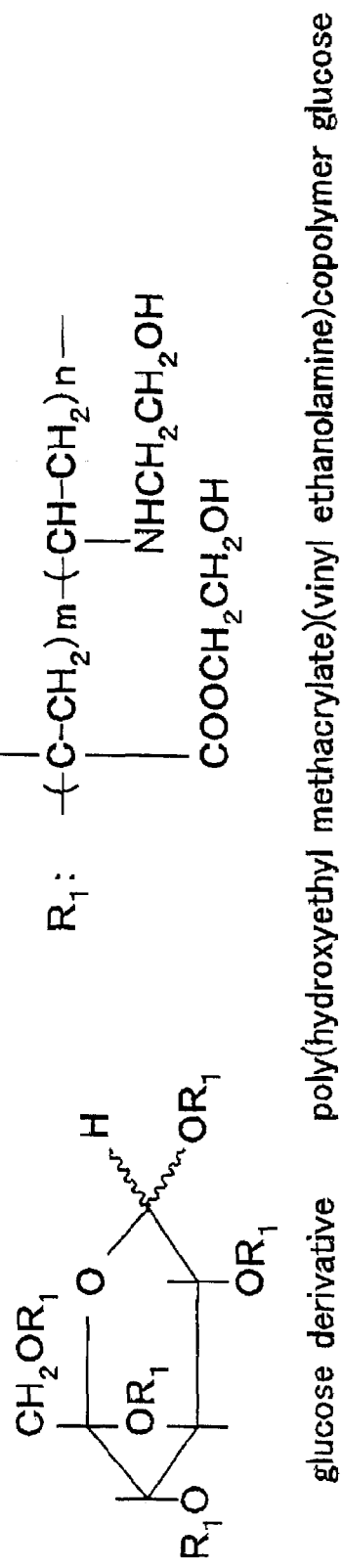

The water-soluble deodorant related to the present invention may contain a deodorant having an effect against, for example, odor and, particularly, urine odor. The water-soluble deodorant may contain a compound having adsorptive effect against aldehydes and lower fatty acids and so on, which are thought to be urine components (for example, the anion exchange group [an amino group ($-NH_2$) and so on]), and having adsorptive effect against amines and ammonia, which are thought to be urine components (for example, the cation exchange group [a carboxyl group ($-COOH$), a sulfonic acid group ($-SO_3H$) and so on]). Specifically, the water-soluble deodorant may contain substance (for example, poly(acrylic acid)(allylsulfonic acid) copolymer glucose, poly(hydroxyethyl methacrylate)(vinyl ethanolamine) copolymer glucose), which is obtained by radioactive-ray graft polymerization using starting materials such as acrylic acid, sodium allylsulfonate, glucose, 2-ethanolamine, 2-hydroxyethylmethacrylate and so on. Further, the water-soluble deodorant may contain an ion-exchange type deodorant, which is produced by the radioactive-ray raft polymerization. The ion-exchange type deodorant may contain a compound obtained by the radioactive-ray graft polymerization, and may contain, for example, poly(acrylic acid)(allylsulfonic acid) copolymer glucose, which is a liquid cation exchange body, and poly(hydroxyethyl methacrylate)(vinyl ethanolamine) copolymer glucose, which is a liquid anion exchange body. Further, it may contain an ion exchange type deodorant obtained by radioactive-ray graft copolymerization. The ion exchange type deodorant may contain a compound obtained by radioactive-ray graft copolymerization, and, for example, may contain poly(acrylic acid)(allylsulfonic acid) copolymer glucose, which is a liquid cation exchange ion exchange body, and poly(hydroxyethyl methacrylate)(vinyl ethanolamine) copolymer glucose. The structural formula of these compounds are shown in FIG. 1(a) and FIG. 1(b). FIG. 1(a) shows an example of poly(acrylic acid)(allylsulfonic acid) copolymer glucose, wherein $R_2$ is a polymer group containing sulfonic acid group and carboxylic group, and glucose is used as monosaccharide. Alternatively, in FIG. 1(a), it is not necessary to substitute the hydrogen atoms of all the hydroxyl groups in the glucose moiety, and it is possible to use a glucose derivative wherein at least one of the hydrogen atoms of the hydroxyl group is replaced by substituent $R_2$. FIG. 1(b) shows an example of poly(hydroxyethyl methacrylate)(vinyl ethanolamine) copolymer glucose wherein $R_1$ is a polymer group containing amine, and glucose is used as monosaccharide. Alternatively, in FIG. 1(b), it is not necessary to substitute the hydrogen atoms of all the hydroxyl groups in the glucose moiety, and it is possible to use a glucose derivative wherein at least one of the hydrogen atoms of the hydroxyl group is replaced by substituent $R_1$. In FIGS. 1(a) and 1(b), m and n independently refer to an integer, respectively.

The deodorant related to the present invention may contain either or both of the ion exchange bodies. When both are contained, it is preferable to provide the deodorant which is not easy to degrade the functions of each of the ion exchange bodies by the mutual interaction of both ion exchange bodies. Incidentally, molecular weights of these deodorants are preferably at least 6000.

Figure 2:
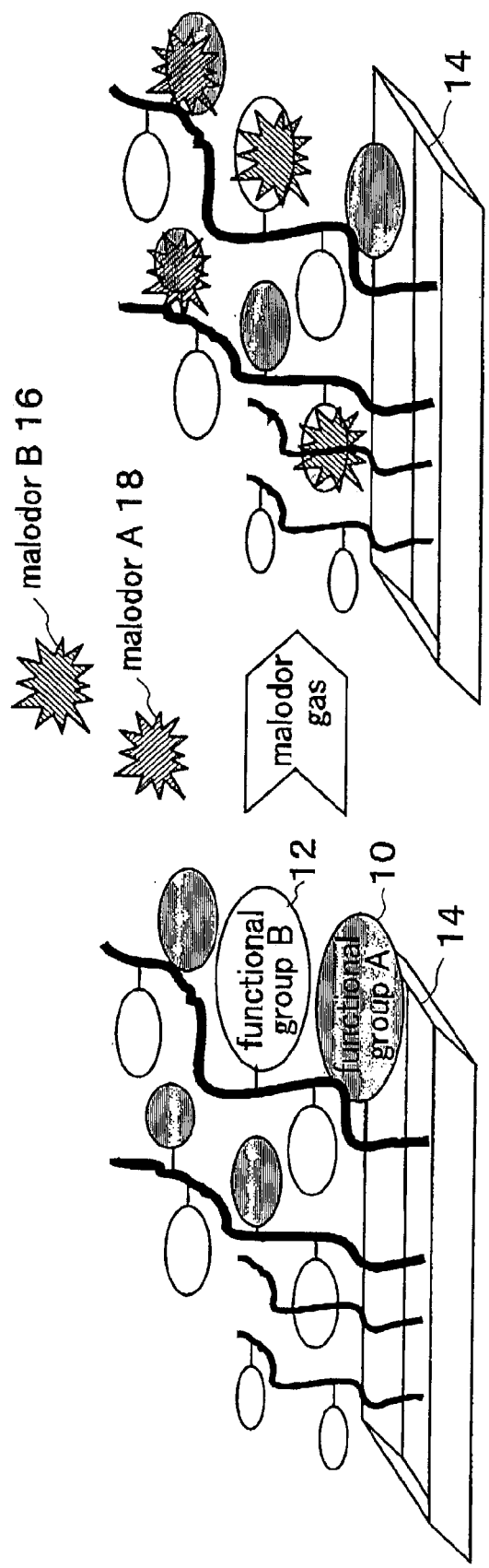
FIG. 2 is a schematic view of describing deodorizing function of deodorants, which may be used in the present invention.

FIG. 2 shows a model to schematically show deodorizing functions of the deodorant at the current stage. In FIG. 2, functional group A and functional group B show different properties, and are capable of adsorbing different malodor gas. Specifically, functional group A and functional group B adsorb malodor A and malodor B, respectively.

FIG. 3 schematically shows chemical formula for illustrating how the deodorant in accordance with the present invention adsorbs amines, lower fatty acids, sulfur compounds and aldehyde. In FIG. 3, $R_1$ and $R_2$ refer to a hydrocarbon moiety. For example, basic compounds such as amines and ammonia are adsorbed as following formula.

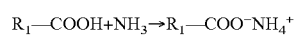

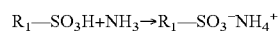

The following formula is given when lower fatty acids are adsorbed.

The following formula is given when lower fatty acids are adsorbed.

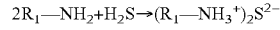

The following formula is given in the case of aldehydes.

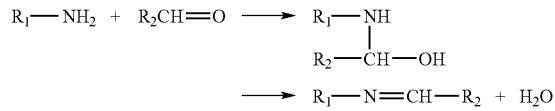

This model is a presumed model at this stage and can suitably explain experimental results mentioned later,

[Hydrophilic Fiber]

The hydrophilic fiber is a fiber that is compatible with water and so on and may contain a fiber having good wettability. The fiber contains a fiber that is wettable and particularly a fiber having a wettable surface. Even though the fiber itself is not made of a hydrophilic material, the hydrophilic fiber contains the fiber that is provided a wettable surface by a surface treatment such as a surfactant processing and other processing.

Specific examples of the aforementioned hydrophilic fiber may be a fiber made of a hydrophilic material such as cellulose fiber, acrylic fiber, acetate fiber, a fiber made of any of the combination thereof and so on. For example, pulp and rayon are representative fibers containing cellulose fiber, and are included in the aforementioned hydrophilic fiber. Particularly, the fiber having water swelling property such as the aforementioned fibers is further preferable.

Such hydrophilic fibers as described above may include those which have been made hydrophilic by treating the surface of synthetic fibers with a surfactant, and also fibers prepared by kneading resin as a raw material for synthetic fiber with surfactant. Examples of these fibers are the polyolefin fiber such as polyethylene, polypropylene, etc., polyester fiber such as polyethylene terephthalate, etc., and polyurethane fiber, etc.

In general, the substrate for deodorant adhesion may be prepared using the above-described hydrophilic fiber as a raw material, and, for example, a material such as tissue in the form of sheet made of hydrophilic fibers such as pulp, rayon or the like may be used as a substrate. Substrates for deodorant adhesion according to the present invention include woven and non-woven fabrics. Methods of preparing non-woven fabric comprise thermal bond, span bond, chemical bond, span lace and air laid methods, and they are appropriately selected paying attention to characteristics of the product to be obtained.

[Coating of Deodorant]

It is possible to coat the deodorant as an undiluted solution to the fiber substrate including the aforementioned fibers, and, when the viscosity adjustment is required, it may be diluted or dispersed in water for coating. Means of coating may include the extrusion coating by spray jet or slot coater, transfer coating with roll coater, gravure coating, and the like, or, fiber substrates including fibers may be dipped in the deodorant which has been adjusted to a suitable concentration for coating. Coating pattern in the case of coating the fiber substrate with deodorant may be that to cover the whole surface of substrate, intermittent coating, or dotty, linear, or checked pattern in consideration of absorbability or economy of the deodorant.

After coating the deodorant or aqueous solution thereof to the fiber substrate including fibers as described above, it is preferable to perform an appropriate treatment such as drying at room temperature, heat drying, etc, to fix the deodorant to fiber substrate including fibers.

In general, the deodorizing function increases with the increase in the amount of deodorant, but, the too much excess thereof is likely to obstruct the water absorbent function and/or permeability of liquid such as body fluid, so that the excessive amount is not necessarily preferable from the economical point of view. On the other hand, when the amount of deodorant is too little, the deodorizing function is likely to be insufficient. As a result of various experiments, the amount of this deodorant is preferably in the range of 0.005~1 g (dry weight) per 100 g held water per one piece of the product, more preferably in the range of 0.01~0.5 g (dry weight). Furthermore, the amount of deodorant is preferably in the range of 0.05~10 parts (dry weight) per 100 weight parts of the hydrophilic fiber substrate (including fiber) prior to coating, and more preferably in the range of 0.5~5 parts (dry weight).

[Arrangement of Absorbent Article]

It is preferable to arrange the absorbent article according to the present invention at the most optimal position to deodorize the odor (e.g. offensive odor, urine stink, etc.), for example, at the position directly in contact with the odor source such as liquid and the like (e.g. urine) or in the vicinity thereof, or, though not too far away from the odor source liquid and the like but near the odor-sensitive nose of humans, etc. and detector and the like, or between the odor source and nose, etc.

For example, in the case where the deodorant is used for the purpose of solving the unpleasant feeling due to the urine odor at the time of diaper exchange, since the urine odor generates (escapes) through the liquid-permeable surface material, it is more preferable to arrange the deodorant in the vicinity where pulp, tissue, etc. used as the absorbent body are present (in the image of the cross section of the absorbent article (the topsheet to the backsheet)), although the deodorant may be arranged at any of the surface material (surface, back), absorbent body (inside, upper layer) and back material (absorbent body side). Furthermore, due to the invention of highly absorbent resin and moisture-permeable leakproof sheet, the diaper these days can be worn for hours at night and while the wearer is out. In such cases, the offensive odor escapes through minute pores of the moisture-permeable leakproof sheet, the place of deodorant arrangement may be any of (1) the surface material (surface, the back), absorbent body (the inside, surface layer) and back material (absorbent body side), and (2) the place near the inside back material of the absorbent body or surface layer of the back material, or absorbent body side of back material (moisture permeable leakproof sheet) are thought to be more effective and preferable for the deodorant function.

To further improve the deodorization efficiency, it is preferable to arrange the deodorant concentrically near the urination part of the wearer (further front side from the center of the absorbent article for men, and the central part thereof for women) (in the image of the absorbent article in the direction of front main section of dress (target side) to rear main section (fasson side).

EXAMPLES

In the following, the sample adjustment that has been specifically performed and assessment results thereof will be described.

[Deodorant Sample]

Ion exchanger type deodorants obtained by the radiation-induced graft copolymerization method invented at the Atomic Energy Research Institute of Japan were used as the deodorant sample. One type contains a liquid cation exchanger, poly(acrylic acid)(allylsulfonic acid) copolymer glucose, and the other type comprises an anion exchanger, poly(hydroxyethyl methacrylate)(vinyl ethanolamine) copolymer glucose. Both of their molecular weights were more than 6,000. The aforementioned two types of copolymers were blended in the ratio of 50 to 50, dissolved in water to give a 5 percent solution, and used in the coating as described below.

In this case, as a comparative example of deodorant was used the non-washed activated carbon product (Nakarai Tech) prepared from saw dust in the powder form of about 350 mesh in particle diameter (hereafter referred to as "activated carbon"). Furthermore, as another comparative example of deodorant, a synthetic zeolite (Union-Showa), "ABSCENTS 3000™" (chemical name: sodium aluminosilicate, $Na_2O$ less than 5 percent, $Al_2O_3$ less than 4 percent, $SiO_2$ less than 100 percent, water less than 10 percent, and 3 to 5 μm in diameter) (hereafter referred to as "zeolite") was used.

[Fiber Substrate]

<Fiber Substrate 1>

A tissue (Kokko Papermaking Co. Ltd., Japan) in the sheet form prepared from 100 percent wood pulp as a raw material was used as the fiber substrate 1. The weight thereof per unit area was 18.5 g/m².

<Fiber Substrate 2>

A thermal bond non-woven fabric comprising PE (polyethylene)/PET (polyethylene terephthalate) bi-component fiber (Unicharm Co., Sofron™, hereinafter referred to as TA non-woven fabric (hydrophilic)) was used as the fiber substrate 2. This substrate is composed of PE/PET bi-component fiber of 25 g/m$^2$, whose surface has been treated with a surfactant <Fiber Substrate 3>

The above-described thermal bond non-woven fabric comprising PE/PET bi-component fiber was immersed into distilled water for 1 hour, washed thrice with distilled water, then dried at room temperature for 24 hours, and used as the fiber substrate 3 (hereafter referred to as TA non-woven fabric (hydrophobic)).

[Coating with Deodorant]

One, two, four and eight sheets of the above-described substrate 1 (100 mm×300 mm) were laid one on top of another to prepare the fiber substrates for coating 1-1, 1-2, 1-4 and 1-8. The aforementioned substrates 2 and 3 were also similarly laminated to prepare the substrates for coating 2-1, 2-2, 2-4 and 2-8 and 3-1, 3-2, 3-4 and 3-8, respectively. To these substrates thus prepared was sprayed the above-described 5 percent deodorant aqueous solution using a hand sprayer at the predetermined amounts (0.9 and 3.0 g). Then, the sprayed substrates were dried at 50° C. for 2 hours, and used as the experimental samples for deodorant coating, 1-1, 1-2, 1-4 and 1-8; 2-1, 2-2, 2-4 and 2-8; and 3-1, 3-2, 3-4 and 3-8.

In the case of coating the substrate 4 with the deodorant a predetermined amount thereof was sprayed successively from the topsheet using a hand sprayer, and then dried at 50° C. for 2 hours. In the case of applying the deodorant of comparative example, activated carbon and zeolite, to the substrate 4, predetermined amount thereof (0.5 g) was weighed in a piece of powder paper, and sprayed so as to be homogeneous successively from the topsheet.

[Experiment 1]

Using a filter paper [No. 2 (Toyo Roshi Co. Ltd.)] of 50×100 mm in size as an absorbent body (absorbent), the above-described deodorant-coated samples (1-1, 1-2, 1-4, 1-8; 2-1, 2-2, 2-4, 2-8; 3-1, 3-2, 3-4, 3-8) cut into a size of 50×100 mm were laid over said absorbent body. Aliquot (10 g each) of the fresh urine sample collected from a healthy normal subject was poured to the central part of the above-described sample set, which was enclosed in a polypropylene bag provided with a zipper (PP bag provided with a zipper (Minigrip) (Seisan Nippon)), left at standing at 37° C. for 1, 2, 4 and 8 hours. Odor levels of said sample sets were confirmed by a panel of five healthy normal adults using a method of odor grading according to six ranks. In this method of odor grading according to six ranks, odor levels are assessed according to the following six ranks: "0: no odor (odorless), 1: barely detectable odor, 2: weak odor but identifiable of its source, 3: easily detectable odor, 4: strong odor, 5: intense odor."

[Results of Experiment 1]

Results of the sensory assessment test are summarized in Table 1 representing the means of grades assessed by five subjects. It was revealed that, in comparison of deodorizing effects of hydrophilic fiber assemblies such as tissue [substrate 1] and TA non-woven fabric (hydrophilic) [substrate 2] to that of TA non-woven fabric (hydrophobic) [substrate 3], tissue and TA woven fabric (hydrophilic) were more highly effective than TA non-woven fabric (hydrophobic).

TABLE 1

Results of Experiment 1

| Sample No. | No. of overlapping sheets (sheet) | amount of spray (g) | METSUKE after drying (g/m$^2$) | deodorizing effect (elapsed time [hour]) | | | |
|---|---|---|---|---|---|---|---|
| | | | | 1 | 2 | 4 | 8 |
| 1-1 | 1 | 0.9 | 1.5 | 3.0 | 2.6 | 2.8 | 2.8 |
| 1-2 | 2 | 0.9 | 1.5 | 2.6 | 2.4 | 2.6 | 2.8 |
| 1-4 | 4 | 0.9 | 1.5 | 1.8 | 1.8 | 1.8 | 2.0 |
| 1-8 | 8 | 0.9 | 1.5 | 1.6 | 1.4 | 1.6 | 1.6 |
| 1-1 | 1 | 3.0 | 5.0 | 2.0 | 2.6 | 2.4 | 2.2 |
| 1-2 | 2 | 3.0 | 5.0 | 1.8 | 2.0 | 2.0 | 2.2 |
| 1-4 | 4 | 3.0 | 5.0 | 1.4 | 1.2 | 1.4 | 1.8 |
| 1-8 | 8 | 3.0 | 5.0 | 1.0 | 1.0 | 1.2 | 1.8 |
| 2-1 | 1 | 0.9 | 1.5 | 3.0 | 2.6 | 3.0 | 3.0 |
| 2-2 | 2 | 0.9 | 1.5 | 2.8 | 2.4 | 2.6 | 3.0 |
| 2-4 | 4 | 0.9 | 1.5 | 2.2 | 2.0 | 2.0 | 3.0 |
| 2-8 | 8 | 0.9 | 1.5 | 1.6 | 1.4 | 1.6 | 2.0 |
| 2-1 | 1 | 3.0 | 5.0 | 3.0 | 2.8 | 2.4 | 3.0 |
| 2-2 | 2 | 3.0 | 5.0 | 2.8 | 2.2 | 2.2 | 2.0 |
| 2-4 | 4 | 3.0 | 5.0 | 2.0 | 1.2 | 1.4 | 2.0 |
| 2-8 | 8 | 3.0 | 5.0 | 1.6 | 1.0 | 1.2 | 2.0 |
| 3-1 | 1 | 0.9 | 1.5 | 3.6 | 4.0 | 4.4 | 4.8 |
| 3-2 | 2 | 0.9 | 1.5 | 3.4 | 4.0 | 3.5 | 4.8 |
| 3-4 | 4 | 0.9 | 1.5 | 3.0 | 3.4 | 3.2 | 3.8 |
| 3-8 | 8 | 0.9 | 1.5 | 3.0 | 3.2 | 3.2 | 3.8 |
| 3-1 | 1 | 3.0 | 5.0 | 3.2 | 3.4 | 4.2 | 4.6 |
| 3-2 | 2 | 3.0 | 5.0 | 3.0 | 3.2 | 3.4 | 4.0 |
| 3-4 | 4 | 3.0 | 5.0 | 3.0 | 3.0 | 3.0 | 3.6 |
| 3-8 | 8 | 3.0 | 5.0 | 3.0 | 2.8 | 2.8 | 3.2 |
| No Sample | — | — | — | 4.5 | 5.0 | 5.0 | 5.0 |

In Table 1, METSUKE refers to "by a specific weight per unit."

Furthermore, even using the same substrate, deodorizing effects became higher as the number of substrate sheets increase. This is likely to be due to that, even though the amount of deodorant added to each sheet is small, the deodorant is arranged to broadly disperse (spread) into the fabric substrate so as to be able to maximize the deodorizing effect. That is, it is thought that, by spraying the hydrophilic deodorant over a hydrophilic fiber to disperse it into the substrate, the surface area adhered with deodorant within the substrate is increased to show the effect. In addition, this is likely to be due to that, in the substrate, with the increase in the number of laminated sheets, the dispersion (spread) of deodorant in the width direction is increased so as to enlarge the area of deodorant adhesion to elevate the effect.

[Experiment 2]

To measure the deodorizing effect on the basic (dimethylamine), neutral (acetaldehyde) and acidic (butyric acid) substances in the case where the incontinence pad product has been compounded with a deodorant. Experiment 2 was performed as follows.

<Fiber substrate 4>

An incontinence guard having a commercial name of "LIEFREE" pants (Uni-Charm Corporation, Japan) was used as a fiber substrate 4. This product is arranged with the fiber substrate 2 as a surface material, and the absorbent body thereof is composed of the fluff pulp, highly water absorbent polymer tissue.

<Method of Measuring Dimethylamine>
(1) Dimethylamine (50 percent aqueous solution (Nakarai Reagent Co. Ltd.) (4 g) was placed in a 1000-ml Erlenmeyer flask, and adjusted to a 0.2 percent solution wit physiological saline. In this case, to avoid the evaporation of gas, the adjustment was carried out in a 3° C. built-in chamber.
(2) Into a separable flask was placed a sample, and into the central part thereof was poured the solution (100 g) adjusted in (1). As a blank, only the adjusted solution without the sample was poured into the flask. The separable flask was assembled, a rubber stopper was inserted to the central hole, and about 1 l of air was stored in an attached scent bag using a (hypodermic) syringe. A silicone tube attached to the flask was closed using a pinch cock. This flask was heated in a 37° C. thermostat, and, after a predetermined period of time, the gas concentration was measured using a detector tube (Gasteck amines 180).

<Method for Measuring Acetaldehyde>
(1) Acetaldehyde (Nakarai Reagent Co.) (0.1 g) was placed in a 1000-ml Erlenmeyer flask, and adjusted to a 0.01 percent solution with physiological saline. In this case, to avoid the evaporation of gas, the adjustment was carried out in a 3° C. built-in chamber.
(2) Into a separable flask was placed a sample (pad), and into the central part thereof was poured the solution (100 g) adjusted in (1). As a blank, only the adjusted solution without the sample was poured into the flask. The separable flask was assembled, a rubber stopper was inserted to the central hole, and about 1 l of air was stored in an attached scent bag using a (hypodermic) syringe. A silicone tube attached to the flask was closed using a pinch cock. This flask was heated in a 37° C. thermostat, and, after a predetermined period of time, the gas concentration was measured using a detector tube (Gasteck Co. Ltd., acetaldehyde 92M).

<Method of Measuring Butyric Acid>
(1) n-Butyric acid (Nakarai Reagent Co. Ltd.) (3 g) was placed in a 1000-ml Erlenmeyer flask, and adjusted to a 0.2 percent solution with physiological saline. In this case, to avoid the evaporation of gas, the adjustment was carried out in a 3° C. built-in chamber.
(2) Into a separable flask was placed a sample (pad), and into the central part thereof was poured the solution (100 g) adjusted in (1). As a blank, only the adjusted solution without the sample was poured into the flask. The separable flask was assembled, a rubber stopper was inserted to the central hole, and about 1 l of air was stored in an attached scent bag using a (hypodermic) syringe. A silicone tube attached to the flask was closed using a pinch cock. This flask was heated in a 37° C. thermostat, and, after a predetermined period of time, the gas concentration was measured using a detector tube (Gasteck Co. Ltd. acetic acid 81L)

[Results of Experiment 2]

The results of Experiment 2 are summarized in Tables 2 to 8. In the case where the deodorant processing was applied to the product (substrate 4), concentrations of offensive odor gas after 120 min were less than 5 ppm for dimethylamine, less than 85 ppm for acetaldehyde and less than 0.05 ppm for n-butyric acid. Furthermore, the deodorization rates [Deodorization rate (percent)=(gas concentration of the blank−gas concentration of each sample)/gas concentration of the blank×100] were all more than 50 percent for dimethylamine, acetaldehyde and n-butyric acid, while, with activated carbon and zeolite used in Comparative Example, the rates were all less than 50 percent.

TABLE 2

| | | Detected Concentration of Dimethylamine | | | | |
|---|---|---|---|---|---|---|
| | amount of deodorant | elapsed time (minute) | | | | |
| Sample No. | g/sheet | 10 | 30 | 60 | 120 | 180 |
| Vacant | | 122.00 | 220.00 | over detection limit | over detection limit | over detection limit |
| Blank | 0.000 | 71.67 | 58.33 | 26.67 | 11.67 | 0.00 |
| Example 2-1 | 0.045 | 30.00 | 35.33 | 15.00 | 4.67 | 0.00 |
| Example 2-2 | 0.090 | 30.00 | 36.67 | 13.00 | 4.00 | 0.00 |
| Example 2-3 | 0.450 | 16.67 | 23.33 | 8.33 | 0.67 | 0.00 |
| Activated carbon | 0.500 | 52.22 | 44.44 | 15.44 | 6.89 | 0.00 |
| Zeolite | 0.500 | 63.33 | 46.67 | 16.67 | 8.33 | 0.00 |

TABLE 3

Deodorizing Ratio of Dimethylamine

| Sample No. | amount of deodorant g/sheet | elapsed time (minute) | | | | |
|---|---|---|---|---|---|---|
| | | 10 | 30 | 60 | 120 | 180 |
| Example 2-1 | 0.045 | 58.14 | 39.43 | 43.75 | 60.00 | 100.00 |
| Example 2-2 | 0.090 | 58.14 | 37.14 | 51.25 | 65.71 | 100.00 |
| Example 2-3 | 0.450 | 76.74 | 60.00 | 68.75 | 94.29 | 100.00 |
| activated carbon | 0.500 | 23.81 | 23.81 | 42.08 | 40.95 | 100.00 |
| zeolite | 0.500 | 11.63 | 20.00 | 37.50 | 28.57 | 100.00 |

TABLE 4

Detected Concentration of Acetaldehyde

| Sample No. | amount of deodorant g/sheet | elapsed time (minute) | | | | |
|---|---|---|---|---|---|---|
| | | 10 | 30 | 60 | 120 | 180 |
| vacant | | 35.00 | 120.00 | 120.00 | 90.00 | 220.000 |
| blank | 0.000 | 136.67 | 136.67 | 143.33 | 166.67 | 193.33 |
| Example 2-4 | 0.045 | 86.67 | 103.33 | 98.35 | 81.67 | 83.33 |
| Example 2-5 | 0.090 | 51.67 | 70.00 | 73.35 | 53.33 | 53.33 |
| Example 2-6 | 0.450 | 40.00 | 35.00 | 20.00 | 66.67 | 13.33 |
| activated carbon | 0.500 | 100.00 | 101.67 | 103.33 | 92.22 | 101.11 |
| zeolite | 0.500 | 136.67 | 130.00 | 133.33 | 140.00 | 146.67 |

TABLE 5

Deodorizing Ratio of Acetaldehyde

| Sample No. | amount of deodorant g/sheet | elapsed time (minute) | | | | |
|---|---|---|---|---|---|---|
| | | 10 | 30 | 60 | 120 | 180 |
| Example 2-4 | 0.045 | 36.59 | 24.39 | 31.40 | 51.00 | 56.90 |
| Example 2-5 | 0.090 | 62.20 | 48.78 | 48.84 | 68.00 | 72.41 |
| Example 2-6 | 0.450 | 70.73 | 74.39 | 86.05 | 90.00 | 93.10 |
| activated carbon | 0.500 | 26.83 | 25.61 | 27.91 | 44.57 | 47.70 |
| zeolite | 0.500 | 0.00 | 4.88 | 6.98 | 16.00 | 24.14 |

TABLE 6

Detected Concentration of n-Butyric Acid

| Sample No. | amount of deodorant g/sheet | elapsed time (minute) | | | | |
|---|---|---|---|---|---|---|
| | | 10 | 30 | 60 | 120 | 160 |
| vacant | | 0.25 | 1.00 | 1.50 | 1.00 | 0.500 |
| blank | 0.000 | 0.87 | 1.00 | 1.30 | 0.92 | 0.92 |
| Example 2-7 | 0.045 | 0.30 | 0.42 | 0.17 | 0.05 | 0.05 |
| Example 2-8 | 0.090 | 0.42 | 0.30 | 0.17 | 0.05 | 0.05 |
| Example 2-9 | 0.450 | 0.32 | 0.27 | 0.08 | 0.02 | 0.02 |
| activated carbon | 0.500 | 0.61 | 0.67 | 0.43 | 0.59 | 0.42 |
| zeolite | 0.500 | 0.77 | 0.83 | 1.15 | 0.83 | 0.83 |

TABLE 7

Deodorizing Ratio of n-Butyric Acid

| Sample No. | amount of deodorant g/sheet | elapsed time (minute) | | | | |
|---|---|---|---|---|---|---|
| | | 10 | 30 | 60 | 120 | 180 |
| Example 2-7 | 0.045 | 65.38 | 58.33 | 87.18 | 94.55 | 94.55 |
| Example 2-8 | 0.090 | 51.92 | 70.00 | 87.18 | 94.55 | 94.55 |
| Example 2-9 | 0.450 | 63.68 | 73.33 | 93.59 | 98.18 | 98.18 |
| activated carbon | 0.500 | 30.13 | 32.18 | 28.63 | 35.76 | 53.94 |
| zeolite | 0.500 | 11.54 | 16.67 | 11.54 | 9.09 | 9.09 |

TABLE 8

Summary of Experiment 2

| dimethylamine | | acetaldehyde | | n-butyric acid | |
|---|---|---|---|---|---|
| Example 2-1 | ○ | Example 2-4 | ○ | Example 2-7 | ○ |
| Example 2-2 | ○ | Example 2-5 | ○ | Example 2-8 | ○ |
| Example 2-3 | ○ | Example 2-6 | ○ | Example 2-9 | ○ |
| activated carbon | Δ | activated carbon | Δ | activated carbon | Δ |
| zeolite | Δ | zeolite | X | zeolite | X |

Note:
With regard to the deodorizing ratio after a period of 2 hours,
"○" refers to the deodorizing ratio of at least 50 percent;
"Δ" refers to the deodorizing ratio ranging from 20 to 50 percent; and
"X" refers to the deodorizing ratio of not more than 20 percent.

[Experiment 3]

To the central part of the above-described deodorant-coated samples (pads) prepared using the substrate 4 were poured aliquots (100 ml) of a fresh urine sample collected from a healthy normal subject, and each sample was placed in a 100-ml beaker, and tightly enclosed in a polypropylene bag provided with a zipper, left at standing at 37° C. for 1, 2, 4 and 8 hours. Odor levels of the sample sets were confirmed by a panel of three healthy normal adults using a method of odor grading according to the following six ranks.

"0: no odor (odorless), 1: barely detectable odor, 2: weak odor but identifiable of its source, 3: easily detectable odor, 4: strong odor, 5: intense odor."

The experimental results are summarized in Table 9. In the present example, all samples show higher deodorizing effects than activated carbon and zeolite.

TABLE 9

Results of Experiment 3

| Sample No. | amount of deodorant g/sheet | elapsed time (minute) | | | |
|---|---|---|---|---|---|
| | | 1 | 2 | 4 | 8 |
| blank | 0.000 | 3.6 | 3.8 | 4.6 | 4.8 |
| Example 3-1 | 0.045 | 3 | 2.4 | 2 | 2.2 |
| Example 3-2 | 0.090 | 3 | 2 | 1.6 | 1.8 |
| Example 3-3 | 0.450 | 2.8 | 1.2 | 1.2 | 1.4 |
| activated carbon | 0.500 | 3.4 | 3.6 | 4 | 4.2 |
| zeolite | 0.500 | 3.4 | 3.6 | 4.6 | 4.6 |

Figure 4:
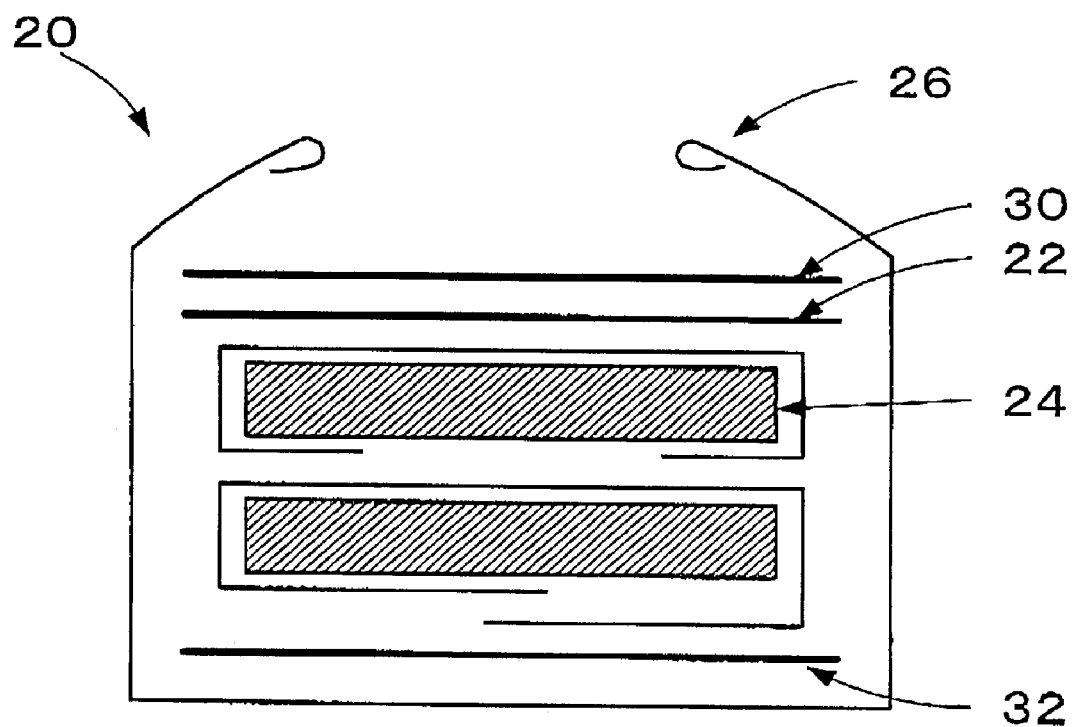
FIG. 4 is a cross-sectional view of one embodiment of an absorbent article in accordance with the present invention.

FIG. 4 shows one example of a product made by applying an absorbent article according to the present invention. This figure is a schematic representation of the cross section of said product. This product is the diaper 20, and constituted by arranging the absorbent body 24 comprising the upper layer pulp and blend SAP in the central part, the upper layer tissue 22 coated with a deodorant according to the present invention over the upper surface of the absorbent body 24, the cushion non-woven fabric 30 further over the upper layer tissue 22, and the backsheet (back film) 32 under the absorbent body 24. This product is so constituted that the odorous component generated from a liquid such as urine and the like which has been absorbed by the absorbent body 24 is absorbed by the deodorant of the tissue 22 so that the odorous component is hardly released upwards, thereby a sufficient deodorizing function being manifested. Furthermore, the back film 32 restricts the downward release of odor so that, as a whole, a diaper having a sufficient deodorizing function can be obtained.

Figure 5:
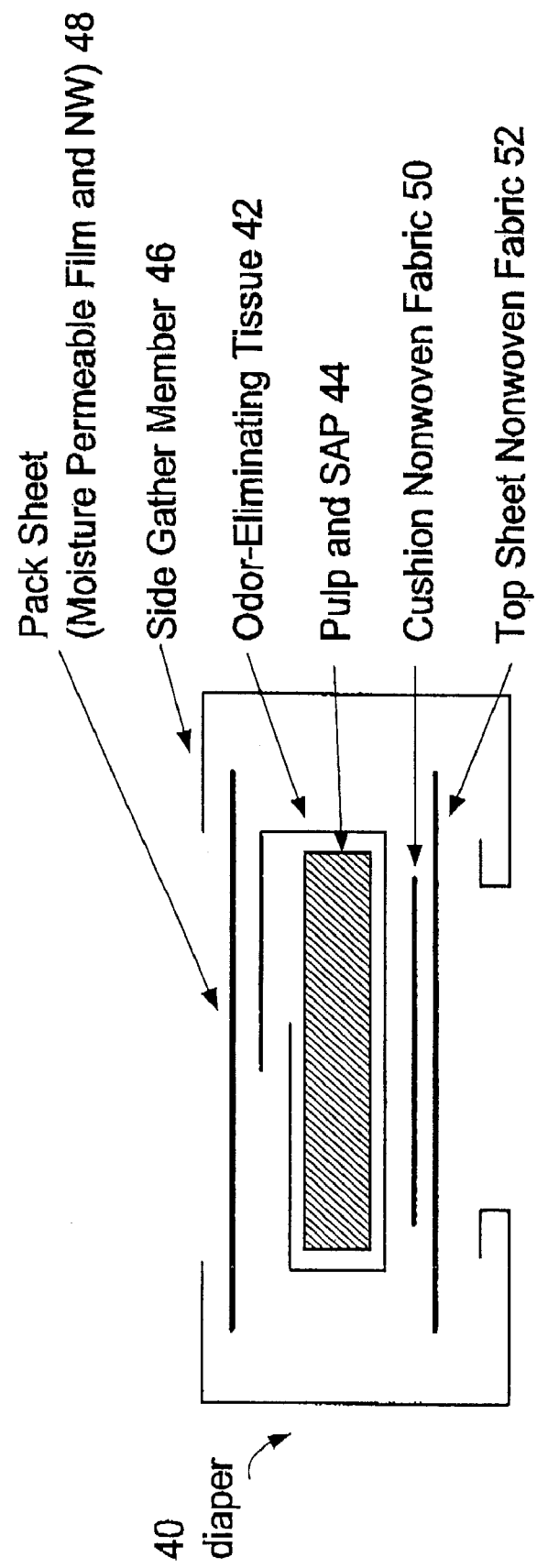
FIG. 5 is a cross-sectional view of another embodiment of an absorbent article in accordance with the present invention.
Figure 6:
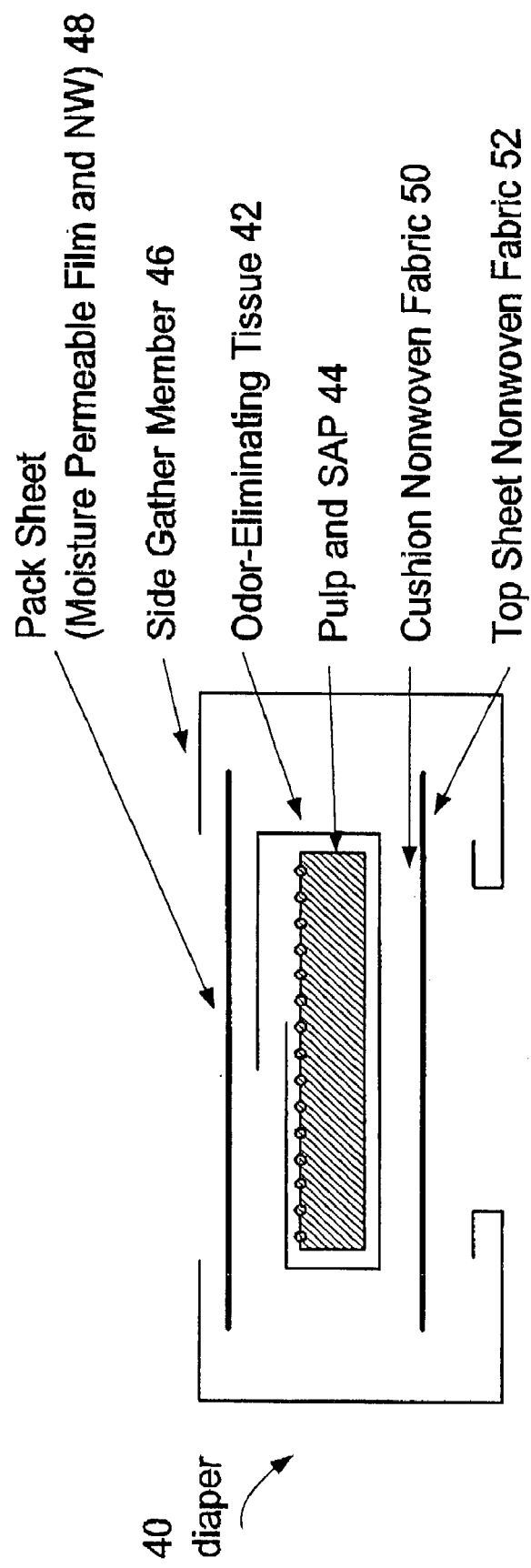
FIG. 6 is a cross-sectional view of another embodiment of an absorbent article in accordance with the present invention.

FIGS. 5 and 6 are the schematic representations of two examples of the products made by applying the absorbent article of the present invention. FIG. 5 schematically represents the cross section of a diaper with the packaging sheet 42 whose entire surface has been coated with the deodorant, while FIG. 6 shows that with the tissue 42 entirely sprayed with the deodorant from underneath, respectively. Since the diapers themselves are both similarly constituted, they will be commonly explained as follows. They are constituted in such a way that the absorbent body 44 is wrapped with the above-described packaging sheet 42, the cushion non-woven fabric 50 and topsheet non-woven fabric 52 are arranged underneath of 42, and the backsheet 48 is arranged over the aforementioned absorbent body wrapped in the packaging sheet 42. Over the upper side of the sheet wrapping the entire diaper, and on the both sides of the absorbent body 44 wrapped in the above-described deodorizing packaging sheet 42 is arranged the side gathers material 46.

In either of diapers in FIGS. 5 and 6, the odorous component generated from a liquid such as urine and the like once absorbed in the absorbent body 44 is trapped by the deodorant in the packaging sheet 42 so that the odorous component is hardly released to the outside thereof, thereby the deodorizing function being able to be sufficiently manifested.

The absorbent article according to the present invention as described above enables the reduction of the body fluid (urine) odor by the addition of a relatively small amount of deodorant through using a hydrophilic fiber and water-soluble deodorant, thus, it is clearly understood that this article has an extremely excellent deodorization capability compared to conventional an absorbent article with the deodorization capability. It was also found that, in the case of processing the hydrophilic fiber with a water-soluble deodorant, the deodorization capability thereof became higher than in the case of using a hydrophobic fiber.

Thus, making the deodorant that is not directly associated with the liquid absorption effectively function in a small amount can decrease the unfavorable influence on the absorbent function of the absorbent body. Furthermore, since it is unnecessary to supplement any new component to prevent the deodorant from falling off or to immobilize the deodorant, it becomes possible to simplify the manufacturing process, prevent the deterioration of working environment such as heat, recovery of the solvent, and the like, and conduct the economical manufacturing.

What is claimed is:

1. An absorbent article, comprising:
    a hydrophilic fiber processed by a water-soluble deodorant, the water-soluble deodorant comprising:
    at least one selected from the group consisting of poly (acrylic acid) (allylsulfonic acid) copolymer glucose and poly (hydroxyethyl methacrylate) (vinyl ethanolamine) copolymer glucose.

2. The absorbent article, of claim 1, wherein the hydrophilic fiber has a water-retaining amount of at least 1 gram per gram.

3. The absorbent article of claim 1, wherein the water-soluble deodorant is present in an amount of 0.05 to 5 parts dry weight per 100 weight parts of hydrophilic fiber.

4. The absorbent article of claim 1, comprising 100 parts by weight of a hydrophilic fiber substrate and 0.05 to 10 parts by weight of the water-soluble deodorant.

5. The absorbent article of claim 4, wherein the water-soluble deodorant is present in an amount of 0.05 to 5 parts by weight of the water-soluble deodorant.

6. The absorbent article of claim 1, wherein the hydrophilic fiber comprises at least one selected from the group consisting of cellulose fiber, acrylic fiber, acetate fiber, fibrous polyacrylate salt and a combination thereof.

7. The absorbent article of claim 1, wherein the hydrophilic fiber is in a sheet, wherein the sheet is sprayed with a solution of the water soluble deodorant, and wherein plural hydrophilic fiber sheets are stacked.

8. A diaper comprising the absorbent article of claim 1.

* * * * *